Nov. 25, 1975
C. F. ZAIGER
APRICOT TREE
Filed Jan. 9, 1975
Plant Pat. 3,809
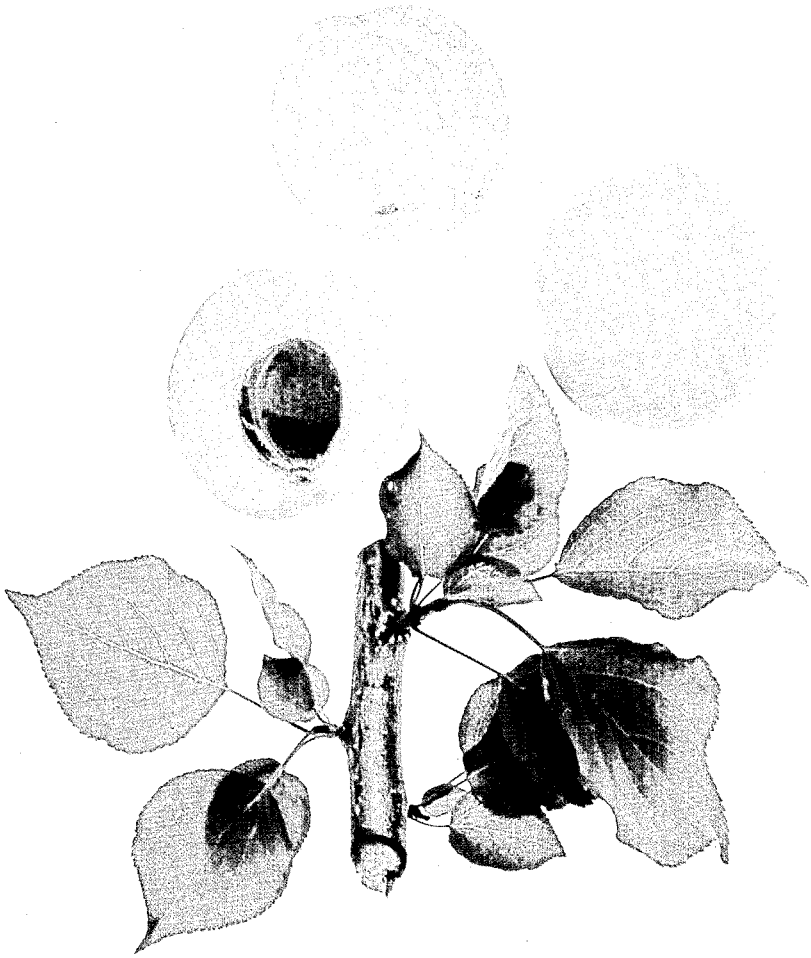

United States Patent

Plant Pat. 3,809

Patented Nov. 25, 1975

3,809

APRICOT TREE

Chris Floyd Zaiger, 537 Rosemore Ave., Modesto, Calif. 95351

Filed Jan. 9, 1975, Ser. No. 539,768

Int. Cl. A01h *5/03*

U.S. Cl. Plt.—39 1 Claim

ABSTRACT OF THE DISCLOSURE

A variety of apricot tree which has the following unique combination of features which are outstanding in a new variety.

1. The large size of the fruit.
2. The coloring of the fruit two weeks before ripening.
3. Even distribution of fruit on the trees.
4. The extreme firmness of the fruit and its good shipping characteristics.
5. The early ripening period of the fruit, occurring in mid to late May.

ORIGIN OF THE VARIETY

The present invention originated by me, in my experimental orchard, located near Modesto, Stanislaus County, Calif., as a selected seedling from a large number of seedlings obtained from Flaming Gold apricot (Pat. 2,822) seeds that had resulted from open-pollinated flowers. These seedlings, which were planted and grown under careful observation by me, gave many and varying characteristics, one such seedling which is the present variety, having been especially desirable with respect to the fruit, was selected for asexual reproduction and commercialization.

ASEXUAL REPRODUCTION OF THE VARIETY

The present variety was asexually reproduced by budding in my experimental orchard near Modesto, Calif. and shows that all characteristics come true to form and are established and transmitted through succeeding propagations.

SUMMARY OF THE VARIETY

The present variety of apricot tree is of large size, vigorous, medium dense, upright growth, productive bearer of large size fruit, early ripening, freestone fruit having firm, yellow flesh and deep yellow skin color. The present variety of apricot tree when compared to Flaming Gold apricot (Pat. 2,822), bears larger fruit; has a more uniform distribution of fruit throughout the tree; a more uniform ripening of fruit throughout the tree, and matures approximately five days earlier. The foregoing characteristics and distinctions definitely differentiate my new variety from its seed parent, as well as from all other varieties of which I am aware.

BRIEF DESCRIPTION OF THE DRAWING

The drawing is an illustration by photographic reproduction in color, of leaves, one whole fruit and a cut half with the stone remaining in place therein.

DESCRIPTION OF THE VARIETY

The botanical details of this new and distinct variety of apricot tree—with color definitions (except those in common color terms) referenced to Reinhold Color Atlas by A. Korneruf and J. H. Wanscher—are as follows:

Tree:
- *Size.*—Large.
- *Vigor.*—Vigorous.
- *Density.*—Medium dense.
- *Productivity.*—Heavy.

Branches: Vigorous, stocky to medium caliper in relationship to length, from smooth to medium roughness.
- *Color.*—Bronze brown (5E5).
- *Lenticels.*—Present.

Trunk:
- *Size.*—Medium stocky.

Leaves:
- *Size.*—Medium. Average length—2½" to 3½". Average width—2" to 3".
- *Form.*—Ovate to orbicular. Pointed. Medium thickness. Relatively smooth.
- *Petiole.*—Average length.
- *Glands.*—Number—1 to 6. Primarily on petiole.
- *Color.*—Under side—28D5. Upper side—28E6.
- *Margin.*—Coarsely serrate.

Flower buds:
- *Size.*—Medium to small.
- *Shape.*—Medium to short, plump.

Flowers:
- *Blooming period.*—Feb. 26, 1974 to Mar. 8, 1974. Varies from year to year due to weather variations.
- *Size.*—Medium.
- *Color.*—White, faint tinge of pink.

Fruit:
- *Shipping ripe.*—Third week of May.
- *Eating ripe.*—Last week of May.
- *Size.*—Large. Axial diameter—from 1⅞" to 2⅝". Transverse diameter in suture plane—2⅜" to 2⅞". Diameter measured at right angles to suture plane—from 1⅝" to 2⅜".
- *Form.*—Slightly variable, usually symmetrical. Globose. At times somewhat compressed laterally toward suture.
- *Suture.*—Usually pronounced from stem to blossom end. Slightly shallower near blossom end. Terminating at blossom end.
- *Cavity.*—From round to somewhat elongated at suture plane, with suture showing on one side. Depth—from about ⅛" to 3/16". Breadth—about ¼".
- *Apex.*—Rounded to slightly depressed.

Skin: Thin, moderately smooth. No tendency to crack. Color is from apricot yellow (5B6) to cadmium orange (5A8). Down—scant, very short.

Flesh:
- *Color.*—Plate 5A8 to 6B8.
- *Flavor.*—Subacid.
- *Texture.*—Firm. Fine. Melting.
- *Fibers.*—Medium size, tender.
- *Ripens.*—Fairly even, slightly earlier at apex.
- *Eating quality.*—Good.

Stone:
- *Type.*—Free. Adheres to flesh somewhat along ventral edge.
- *Size.*—Medium to large. Length—average—1 3/16". Breadth — average — ⅞". Thickness — average—⅝".
- *Form.*—Ovoid.
- *Base.*—Straight.
- *Apex.*—Nearly rounded.
- *Surface.*—Regularly pitted, only slightly throughout.
- *Ridges.*—Two ridges extending approximately 180° across surface of the stone on both sides of the suture plane and approximately 30° displaced from each other.
- *Color.*—Plate 6D6.
- *Splitting tendency.*—None.

The apricot tree and its fruit herein described may vary in slight detail due to climatic and soil conditions under which the variety may be grown; the present description being of the variety as grown near Modesto, Stanislaus County, Calif.

I claim:

1. A new and distinct variety of apricot tree, substantially as herein shown and described, characterized particularly as to novelty by its large fruit, its even distribution of fruit throughout the tree, its short maturity period being five days earlier than Flaming Gold apricot, and the high degree of firmness of fruit when mature providing good shipping characteristics.

No references cited.

ROBERT E. BAGWILL, Primary Examiner